United States Patent
Cho (10) Patent No.: US 11,998,645 B2
(45) Date of Patent: Jun. 4, 2024

(54) TREATMENT TOOL STERILIZER FOR DENTAL HOSPITAL WITH MICRO BUBBLE TYPE OZONE WATER SUPPLY AND STERILIZING METHOD USING THE SAME

(71) Applicant: ANDONG NATIONAL UNIVERSITY INDUSTRY—ACADEMIC COOPERATION FOUNDATION, Gyeongsangbuk-do (KR)

(72) Inventor: Hee Keun Cho, Gyeongsangbuk-do (KR)

(73) Assignee: Andong National University Industry—Academic Cooperation Foundation, Gyeongsangbuk-do (KR)

( * ) Notice: Subject to any disclaimer, the term of this patent is extended or adjusted under 35 U.S.C. 154(b) by 569 days.

(21) Appl. No.: 17/144,500

(22) Filed: Jan. 8, 2021

(65) Prior Publication Data
US 2021/0205486 A1    Jul. 8, 2021

(30) Foreign Application Priority Data

Jan. 8, 2020 (KR) .................. 10-2020-0002776
Jan. 8, 2020 (KR) .................. 10-2020-0002777
Jan. 8, 2020 (KR) .................. 10-2020-0002778

(51) Int. Cl.
*A61L 2/025* (2006.01)
*A61L 2/18* (2006.01)
(Continued)

(52) U.S. Cl.
CPC ............ *A61L 2/025* (2013.01); *A61L 2/183* (2013.01); *A61L 2/26* (2013.01); *B01F 23/231* (2022.01);
(Continued)

(58) Field of Classification Search
CPC .......... A61L 2/10; A61L 9/20; A61L 2202/11; A61L 2202/14; A61L 2202/25;
(Continued)

(56) References Cited

U.S. PATENT DOCUMENTS 5,347,336 A * 9/1994 Yamada .................. G03C 5/26
396/626
5,855,856 A * 1/1999 Karlson .................. A61L 2/202
204/176
5,993,749 A * 11/1999 Adams .................... C02F 1/481
422/186.01

FOREIGN PATENT DOCUMENTS

JP    2787464 B2    8/1988
JP    2004024926 A    1/2004
(Continued)

OTHER PUBLICATIONS

English machine translation of KR1020110064331 (Year: 2011).*
(Continued)

*Primary Examiner* — Regina M Yoo
(74) *Attorney, Agent, or Firm* — Berkeley Law & Technology Group, LLP (57) ABSTRACT

The present disclosure relates to a treatment tool sterilizer with a micro bubble type ozone water supply. The treatment tool sterilizer includes a sterilization tub configured to accommodate an object to be sterilized; a fresh water supply; an ozone water supply including a pressure pump configured to pressurize and transfer fresh water, an ozone generator, a mixer configured to mix fresh water and ozone, and a bubble generator connected to the mixer and configured to pass fresh water and ozone through the bubble generator so as to form micro bubbles; an ultrasonic generator; a drain; a heater mounted on the sterilization tub and
(Continued)

configured to apply heat in the sterilization tub; and a controller configured to output a control signal.

8 Claims, 6 Drawing Sheets

(51) Int. Cl.
| | | |
|---|---|---|
| *A61L 2/26* | (2006.01) | |
| *B01F 23/231* | (2022.01) | |
| *B01F 23/232* | (2022.01) | |
| *B01F 25/60* | (2022.01) | |
| *C02F 1/00* | (2023.01) | |
| *C02F 1/36* | (2023.01) | |
| *C02F 1/78* | (2023.01) | |
| *A61C 19/00* | (2006.01) | |
| *A61L 101/02* | (2006.01) | |
| *B01F 23/237* | (2022.01) | |
| *B01F 23/2373* | (2022.01) | |
| *B01F 101/00* | (2022.01) | |

(52) U.S. Cl.
CPC .......... *B01F 23/232* (2022.01); *B01F 25/60* (2022.01); *C02F 1/001* (2013.01); *C02F 1/36* (2013.01); *C02F 1/78* (2013.01); *A61C 19/002* (2013.01); *A61L 2101/02* (2020.08); *A61L 2202/11* (2013.01); *A61L 2202/121* (2013.01); *A61L 2202/122* (2013.01); *A61L 2202/14* (2013.01); *A61L 2202/15* (2013.01); *A61L 2202/24* (2013.01); *B01F 23/2373* (2022.01); *B01F 23/237613* (2022.01); *B01F 2101/305* (2022.01); *C02F 2201/006* (2013.01); *C02F 2201/782* (2013.01); *C02F 2303/04* (2013.01); *C02F 2303/18* (2013.01)

(58) Field of Classification Search
CPC ...... A61L 2209/111; B60N 2/002; B60S 1/64; B62D 1/06; E05B 77/54; G02F 1/13306; G02F 1/172
See application file for complete search history.

(56) References Cited

FOREIGN PATENT DOCUMENTS

| | | |
|---|---|---|
| JP | 2018057681 A | 4/2018 |
| KR | 1020000037882 A | 7/2000 |
| KR | 200216082 Y1 | 12/2000 |
| KR | 1007451590000 B1 | 7/2007 |
| KR | 2020090009274 U | 7/2009 |
| KR | 1020090120872 A | 12/2009 |
| KR | 1011216780000 B1 | 2/2012 |
| KR | 1012068190000 B1 | 11/2012 |
| KR | 1016910160000 B1 | 12/2016 |
| KR | 1020190051419 A | 5/2019 |

OTHER PUBLICATIONS

English machine translation of KR1020010015150 (Year: 2001).*
Request for the Submission of an Opinion (Office Action), App. No. KR10-2020-0002776, dated May 26, 2021, 8 pages.
Request for the Submission of an Opinion (Office Action), App. No. KR10-2020-0002777, dated May 26, 2021, 8 pages.
Written Decision on Registration, (Notice of Allowance), App. No. KR10-2020-0002777, dated Jan. 22, 2022, 3 pages.
Request for the Submission of an Opinion (Office Action), App. No. KR10-2020-0002778, dated Jun. 22, 2021, 9 pages.
Written Decision on Registration, (Notice of Allowance), App. No. KR10-2020-0002778, dated Aug. 30, 2021, 4 pages.

* cited by examiner

TREATMENT TOOL STERILIZER FOR DENTAL HOSPITAL WITH MICRO BUBBLE TYPE OZONE WATER SUPPLY AND STERILIZING METHOD USING THE SAME

CROSS-REFERENCE TO RELATED APPLICATION

The present application claims benefits of priorities to Korean Patent Application No. 10-2020-0002776, entitled "STERILIZING DEVICE FOR DENTAL TOOL," Korean Patent Application No. 10-2020-0002777, entitled "STERILIZATION METHOD OF TREATMENT TOOL FOR DENTAL HOSPITAL," and Korean Patent Application No. 10-2020-0002778, entitled "TREATMENT TOOL STERILIZER FOR DENTAL HOSPITAL WITH MICRO BUBBLE TYPE OZONE WATER SUPPLY," filed on Jan. 8, 2020, in the Korean Intellectual Property Office, the entire disclosures of which are incorporated herein by reference.

FIELD

The present disclosure relates to a sterilizer for various treatment tools used in a dental hospital. More specifically, the present disclosure relates to a treatment tool sterilizer for a dental hospital with a micro bubble type ozone water supply which is capable of sterilizing by high concentration ozone water by forming micro bubbles in ozone water, and a sterilizing method using the same.

BACKGROUND

Since treatment tools used in dental hospitals, except for disposable items, are used by several people, there is a high risk of infection with fatal diseases such as hepatitis or AIDS, for example. Therefore, these treatment tools need to be sterilized after use. In particular, for example, burs or scalers used for tooth preparation or polishing are inevitably stained with blood as well as tooth microstructure or saliva of the patient when teeth are ground, so the sterilization of such treatment tools is even more important.

Among various pieces of equipment for sterilizing dental treatment tools, an autoclave has the principle of sterilizing microorganisms with saturated water vapor of high temperature and high pressure. The time to sterilize an object with the autoclave varies depending on the case, but is about 20 to 30 minutes, which is thus not a short time.

Since the treatment tools are not available while the autoclave is operating, hospitals with many patients are equipped with a plurality of sets of treatment tools. In other words, these hospitals are equipped with many handpieces and various treatment tools, and use them alternately. However, since small-scale dental hospitals may not have a large number of rather expensive handpieces, these hospitals often set the operating time of the autoclave to be short. That is, disinfection is done only formally. In hospitals that do not even have the autoclave equipment, tools that need to be sterilized are disinfected only by ultrasonic disinfection or by wiping with an alcohol swab.

RELATED ART DOCUMENTS

RELATED ART 1: Korean Patent Registration No. 10-1121678 (DENTAL HANDPIECE STERILIZER)
RELATED ART 2: Korean Patent Registration No. 10-1206819 (STERILIZED APPARATUS OF DENTAL TOOL)
RELATED ART 3: Korean Patent Registration No. 10-1691016 (OZON STERILIZER FOR DENTAL CLINIC)

SUMMARY

The present disclosure is directed to providing a treatment tool sterilizer for a dental hospital with a micro bubble type ozone water supply. The treatment tool sterilizer according to the present disclosure has excellent practical applicability because it is inexpensive and is not large in size, so it may be installed in a treatment room and used whenever necessary, and uses high concentration ozone water, so the time required for sterilization is short.

A treatment tool sterilizer for a dental hospital with a micro bubble type ozone water supply according to an embodiment of the present disclosure may include: a sterilization tub having a container configured to accommodate an object to be sterilized and a sealing cover covering the container; a fresh water supply configured to supply fresh water into the sterilization tub; an ozone water supply configured to supply ozone water for sterilization into the sterilization tub, wherein the ozone water supply includes a pressure pump configured to pressurize and transfer fresh water provided from the outside, an ozone generator configured to generate ozone, a mixer configured to mix fresh water and ozone transferred by the pressure pump, and a bubble generator connected to the mixer and configured to increase a dissolution concentration of ozone in fresh water by passing fresh water and ozone through the bubble generator so as to form micro bubbles; an ultrasonic generator configured to apply ultrasonic energy to fresh water when fresh water has been filled in the sterilization tub, so that the object to be sterilized immersed in the fresh water is sterilized by ultrasonic energy; a drain configured to discharge water from the sterilization tub; a heater mounted on the sterilization tub and configured to apply heat in the sterilization tub; and a controller configured to output a control signal.

In addition, a circulation pump configured to stir the accommodated fresh water or ozone water is further installed in the sterilization tub.

In addition, a drying heater configured to dry the object to be sterilized after draining the fresh water or ozone water is further provided in the sterilization tub.

In addition, the bubble generator includes: a housing providing a space; a bubble generating cartridge mounted in the space of the housing and configured to pass a mixture of fresh water and ozone through the bubble generating cartridge so as to form micro bubbles; and a sealing cap coupled to the housing to fix the bubble generating cartridge in the housing.

In addition, the bubble generating cartridge includes: a pair of holding cases that are mutually coupled and take the form of a cylinder in which both ends are opened, a Teflon body mounted in the holding cases and having a plurality of micropores through which the mixture of fresh water and ozone passes, and a filter installed upstream of the Teflon body.

In addition, the Teflon body takes the form of a disk having a predetermined thickness, and a plurality of Teflon bodies are arranged in series to be spaced apart by a predetermined distance, and the micropores are formed in each of the Teflon bodies, wherein an inner diameter of the micropores is larger in downstream Teflon bodies than in upstream Teflon bodies.

According to embodiments of the present disclosure, the treatment tool sterilizer for a dental hospital with the micro bubble type ozone water supply is capable of both ultrasonic sterilization and ozone water sterilization, is simple to use, and is particularly excellent in practical applicability due to its short sterilization time.

In addition, the treatment tool sterilizer according to the present disclosure is simple in structure, inexpensive, and not large in size, so it may be installed in a treatment room and used whenever necessary. In addition, according to the method of sterilizing the treatment tool for a dental hospital of the present disclosure, the ultrasonic sterilization and ozone water sterilization may be sequentially performed and high concentration ozone water produced using the bubble generator is applied for sterilization, resulting in short sterilization time and good sterilization efficiency.

DETAILED DESCRIPTION

Hereinafter, embodiments according to the present disclosure will be described in more detail with reference to the accompanying drawings.

Basically, a treatment tool sterilizer for a dental hospital with a micro bubble type ozone water supply according to the present disclosure may sterilize various tools commonly used in dental hospitals simply and effectively and within a short time.

According to an embodiment of the present disclosure, the treatment tool sterilizer includes: a sterilization tub having a container configured to accommodate an object to be sterilized and a sealing cover covering the container; a fresh water supply configured to supply fresh water into the sterilization tub; an ozone water supply configured to supply ozone water for sterilization into the sterilization tub, wherein the ozone water supply includes a pressure pump configured to pressurize and transfer fresh water provided from the outside, an ozone generator configured to generate ozone, a mixer configured to mix fresh water and ozone transferred by the pressure pump, and a bubble generator connected to the mixer and configured to increase a dissolution concentration of ozone in fresh water by passing fresh water and ozone through the bubble generator so as to form micro bubbles; an ultrasonic generator configured to apply ultrasonic energy to fresh water when fresh water has been filled in the sterilization tub, so that the object to be sterilized immersed in the fresh water is sterilized by ultrasonic energy; a drain configured to discharge water from the sterilization tub; a heater mounted on the sterilization tub and configured to apply heat in the sterilization tub; and a controller configured to output a control signal.

According to another embodiment of the present disclosure, the treatment tool sterilizer may include the following as a basic configuration: a sterilization tub having a container configured to accommodate an object to be sterilized and a sealing cover sealing the container; a fresh water supply configured to supply fresh water into the sterilization tub; an ozone water supply configured to supply ozone water into the sterilization tub; a drain configured to discharge water from the sterilization tub; an ultrasonic generator configured to apply ultrasonic energy to fresh water when fresh water has been filled in the sterilization tub, so that the object to be sterilized immersed in the fresh water is sterilized by ultrasonic energy; a heater mounted on the sterilization tub and configured to apply heat in the sterilization tub; and a controller configured to output a control signal.

In addition, a method of sterilizing a treatment tool for a dental hospital of the present disclosure sterilizes an object to be sterilized using a treatment tool sterilizer including the following: a sterilization tub configured to accommodate an object to be sterilized and to be opened or closed, a fresh water supply configured to supply fresh water into the sterilization tub, an ozone water supply configured to supply ozone water into the sterilization tub so that the object to be sterilized is sterilized by coming into contact with the ozone water, an ultrasonic generator configured to apply ultrasonic energy into the sterilization tub so that the object to be sterilized is sterilized by ultrasonic energy, and a drain configured to discharge fresh water or ozone water out of the sterilization tub, after the sterilization is completed. The method of sterilizing the treatment tool may include: a positioning step of positioning the object to be sterilized in the sterilization tub; a fresh water supplying step of supplying fresh water into the sterilization tub using the fresh water supply so that the object to be sterilized is immersed in fresh water, after the positioning step is completed; an ultrasonic energy outputting step of applying ultrasonic energy to the object to be sterilized immersed in fresh water through the fresh water supplying step so that the object to be sterilized is sterilized by ultrasonic energy; a first draining step of discharging fresh water which has been used in the sterilization tub out of the sterilization tub, after the ultrasonic energy outputting step is completed; an ozone water supplying step of filling the sterilizing tub that was emptied through the first draining step with ozone water using the ozone water supply so that the object to be sterilized is immersed in the ozone water, thereby allowing sterilization by an ozone component to proceed; a secondary draining step of discharging ozone water from the sterilization tub, after the sterilization by the ozone water is completed; and an object picking up step of picking up the sterilized treatment tool from the sterilization tub, after the secondary draining step is completed.

In addition, a method of sterilizing a treatment tool of the present disclosure sterilizes an object to be sterilized using a treatment tool sterilizer including the following: a sterilization tub configured to accommodate the object to be sterilized and to be opened or closed, a fresh water supply configured to supply fresh water into the sterilization tub, an ozone water supply configured to supply ozone water into the sterilization tub so that the object to be sterilized is sterilized by coming into contact with the ozone water, an ultrasonic generator configured to apply ultrasonic energy into the sterilization tub so that the object to be sterilized is sterilized by ultrasonic energy, and a drain configured to discharge fresh water or ozone water out of the sterilization tub, after the sterilization is completed. The method of sterilizing the treatment tool includes: a positioning step of positioning the object to be sterilized in the sterilization tub; a fresh water supplying step of supplying fresh water into the sterilization tub using the fresh water supply so that the object to be sterilized is immersed in fresh water, after the positioning step is completed; an ultrasonic energy outputting step of applying ultrasonic energy to the object to be sterilized immersed in fresh water through the fresh water supplying step so that the object to be sterilized is sterilized by ultrasonic energy; a first draining step of discharging fresh water which has been used in the sterilization tub out of the sterilization tub, after the ultrasonic energy outputting step is completed; an ozone water supplying step of filling the sterilizing tub that was emptied through the first draining step with ozone water using the ozone water supply so that the object to be sterilized is immersed in ozone water, thereby allowing sterilization by an ozone component to proceed; a secondary draining step of discharging ozone water from the sterilization tub, after the sterilization by the ozone water is completed; and an object picking up step of picking up the sterilized treatment tool from the sterilization tub, after the secondary draining step is completed.

Figure 1:
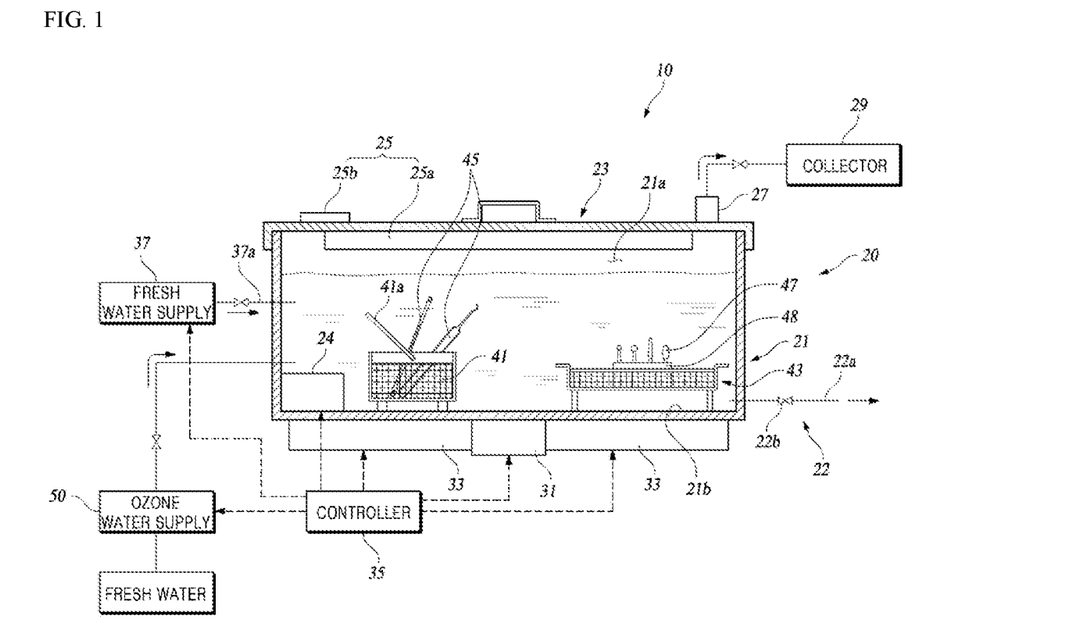
FIG. 1 is a block diagram illustrating an overall structure of a treatment tool sterilizer for a dental hospital with a micro bubble type ozone water supply according to an embodiment of the present disclosure.

FIG. 1 is a block diagram illustrating an overall structure of a treatment tool sterilizer 10 for a dental hospital with a micro bubble type ozone water supply according to an embodiment of the present disclosure.

As shown, the treatment tool sterilizer 10 according to the present embodiment includes a sterilization tub 20, a fresh water supply 37, a micro bubble type ozone water supply 50, an ultrasonic generator 31, a drain 22, a heater 33, a controller 35, a circulation pump 24, a dryer 25, a gas outlet 27, a collector 29, a stainless steel basket 41, and a support tray 43.

The sterilization tub 20 consists of a container 21 and a sealing cover 23, and takes the form of a square box. The sterilization tub 20 may be made of stainless steel. The container 21 provides an accommodating space 21a in which an upper portion is opened. A sterilization process on the object to be sterilized is performed in the accommodating space 21a. The sealing cover 23 covers the top of the container 21 in a manner that may be opened or closed, and serves to seal the accommodating space 21a. If necessary, a silicone or rubber seal may be applied between the container 21 and the sealing cover 23.

In addition, the dryer 25 is mounted on the sealing cover 23. The dryer 25 consists of a drying heater 25a and a switch 25b, and serves to dry the object to be sterilized remaining in the container 21 after draining fresh water or ozone water. The dryer 25 may evaporate moisture on the surface of the object to be sterilized by applying heat to the object to be sterilized. When the drying heater 25a operates, the gas outlet 27 also operates at the same time to discharge moisture in the container 21 to the outside. The type of the drying heater 25a capable of drying the object to be sterilized may be variously changed.

The switch 25b is a manual switch that operates the drying heater 25a. The drying heater 25a may be automatically turned on and off by the controller 35, but may also be manipulated through the switch 25b.

The object to be sterilized is a treatment tool that has been used once, and includes a gripping tool 45 and a bur 47. The gripping tool 45 includes a mirror, a curette, a scaler, tweezers, an explorer, and the like, which are hand held and used by the doctor. The gripping tool 45 has a length enough to be gripped by hand, and is sterilized when put into the stainless steel basket 41. The stainless steel basket 41 is a basket made of stainless steel, and takes the form of a mesh and has a handle 41a to facilitate transport. The size or form of the stainless steel basket 41 may be varied as desired.

In addition, the bur 47 is a grinding tip used by being inserted into a head of a pneumatic handpiece. For the convenience of the sterilization process, the bur 47 may be sterilized when inserted into a bur block 48. The support tray 43 supports the bur block 48 so that the bur block 48 does not contact the bottom surface of the container 21. The support tray 43 is also made of stainless steel and takes the form of a mesh.

During the sterilization process, the gas outlet 27 discharges gas generated in the accommodating space 21a out of the sterilization tub 20, and guides the gas to the collector 29. For example, the gas outlet 27 discharges oxygen generated by heating ozone water, which will be described below, or moisture in the accommodating space 21a during drying. The gas outlet 27 may be a vacuum pump or an exhaust fan.

The collector 29 appropriately processes and exhausts the gas discharged from the sterilization tub 20. For example, if ozone is detected in the collected gas, the collector 29 completely removes the ozone by heating the gas by itself, and discharges the gas into the air.

The fresh water supply 37 is configured to supply purified water into the sterilization tub 20, and is connected to the sterilization tub 20 through a fresh water supply pipe 37a. The supply of fresh water from the fresh water supply 37 is adjusted by the controller 35. That is, the controller 35 may control a supply timing of fresh water, a supply flow rate of fresh water, or the like.

The ozone water supply 50 serves to generate ozone water by dissolving ozone in fresh water provided from the outside, and to supply the generated ozone water into the sterilization tub 20. As is known, ozone has a very strong sterilizing power. Therefore, when ozone is dissolved in water and applied to the object to be sterilized, all kinds of bacteria attached to the object to be sterilized, for example, *Escherichia coli, Shigella*, typhoid bacteria, meningitis, diplococcus, *Staphylococcus aureus*, salmonella bacteria, cold virus, hepatitis, or the like may all be sterilized within a short time.

The ozone water supply 50 includes a pressure pump 51 configured to pressurize and transfer fresh water provided from the outside, an ozone generator 53 configured to generate ozone, a mixer 52 configured to mix fresh water and ozone transferred by the pressure pump, and a bubble generator connected to the mixer 52 and configured to increase a dissolution concentration of ozone in fresh water by passing fresh water and ozone therethrough so as to form micro bubbles. The controller 35 also adjusts the supply of ozone water through the ozone water supply 50. The ozone water supply 50 will be described below with reference to FIGS. 2 to 6.

The ultrasonic generator 20 serves to apply ultrasonic energy to fresh water when fresh water has been filled in the sterilization tub so that the object to be sterilized immersed in the fresh water is sterilized by ultrasonic energy. The vibrational energy of ultrasonic energy applied to fresh water not only sterilizes bacteria attached to the surface of the gripping tool 45 or the bur 47, but also separates foreign substances embedded in fine gaps on the surface of the bur 47. As long as these functions are possible, the installation position of the ultrasonic generator 31 may be changed as necessary.

In one embodiment, the ultrasonic generator 31 is disposed on the lower portion of the container 21, and may output ultrasonic energy when fresh water has been filled in the container 21. The vibrational energy of the ultrasonic energy applied to the fresh water may not only sterilize bacteria attached to the surface of the gripping tool 45 or the bur 47, but also separate foreign substances embedded in fine gaps on the surface of the bur 47. The ultrasonic generator 31 may be installed into the accommodating space 21a, in a sealed state.

The drain 22 discharges water that has been used in the sterilization tub 20, and has a drain pipe 22a and a drain valve 22b. The drain valve 22b is opened or closed by the controller 35. Water that has been used refers to water that has finished the task of ultrasonic sterilization and water that has finished the task of ozone disinfection.

The heater 33 is a heating element fixed to the lower portion, that is, the bottom surface of the bottom portion 21b, of the sterilization tub 20, and heats ozone water after ozone sterilization is completed. Heating ozone water is to remove the ozone component from ozone water that has finished its task. When ozone water is heated, the ozone component in the ozone water is decomposed and converted into oxygen, resulting in water remaining. The remaining water is drained through the drain 22, and oxygen is exhausted through the gas outlet 27.

The heating temperature of the heater 33 may be adjusted as needed by the controller 35. For example, the heater 33 may output heat of about 30° C. to decompose ozone, and boil fresh water to heat and disinfect the object to be sterilized.

In addition, a stirrer may be installed in the sterilization tub 20. The stirrer serves to stir fresh water or ozone water accommodated in the accommodating space 21a, and may include a circulation pump 24. The circulation pump 24 is controlled by the controller 35. Also, the circulation pump 24 may not only mix fresh water or ozone water to be in a uniform state, but may also form a strong water stream, if necessary, so that foreign substances such as bacteria or bone tissue in a sterilized state are more quickly separated from the object to be sterilized.

The circulation pump 24 may not only stir fresh water or ozone water accommodated in the accommodating space 21a to induce fresh water or ozone water to be in a uniform state, but may also form a strong water stream, if necessary so that foreign substances such as bacteria or bone tissue are more quickly separated from the object to be sterilized.

Figure 2:
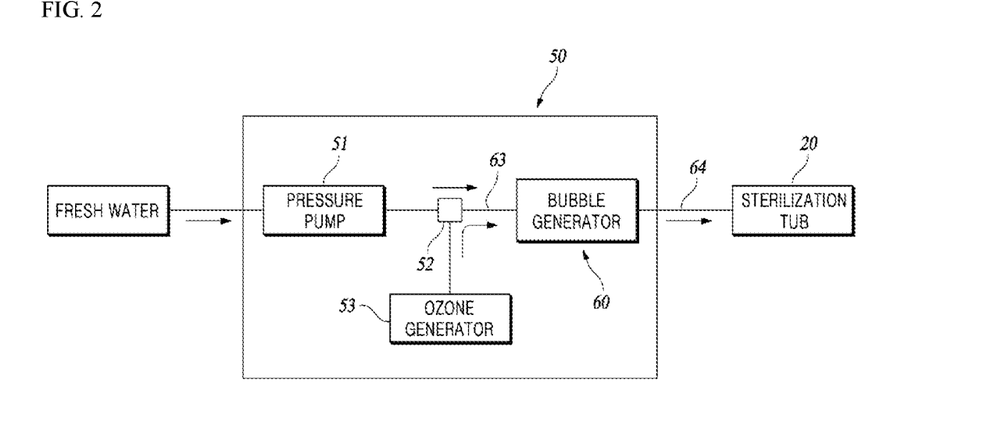
FIG. 2 is a block diagram illustrating a configuration of the ozone water supply shown in FIG. 1.
Figure 3:
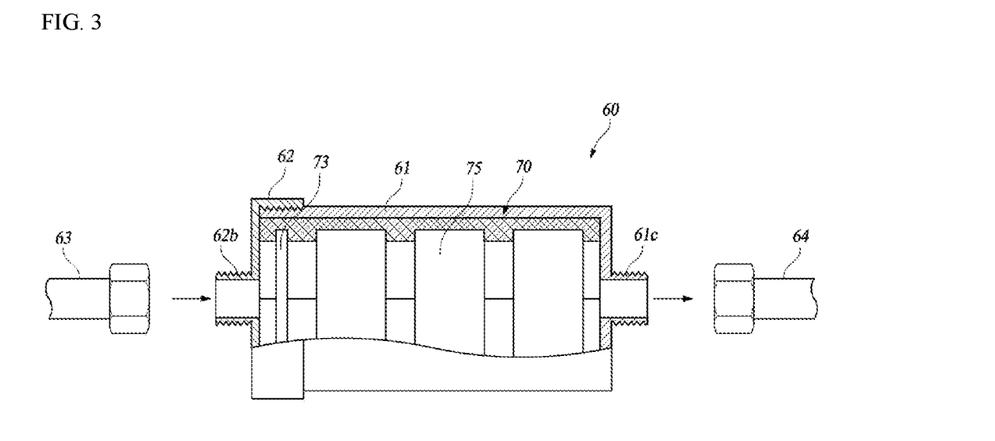
FIG. 3 is a partially cut-away cross-sectional view illustrating an internal structure of the micro bubble generator of FIG. 2.
Figure 4:
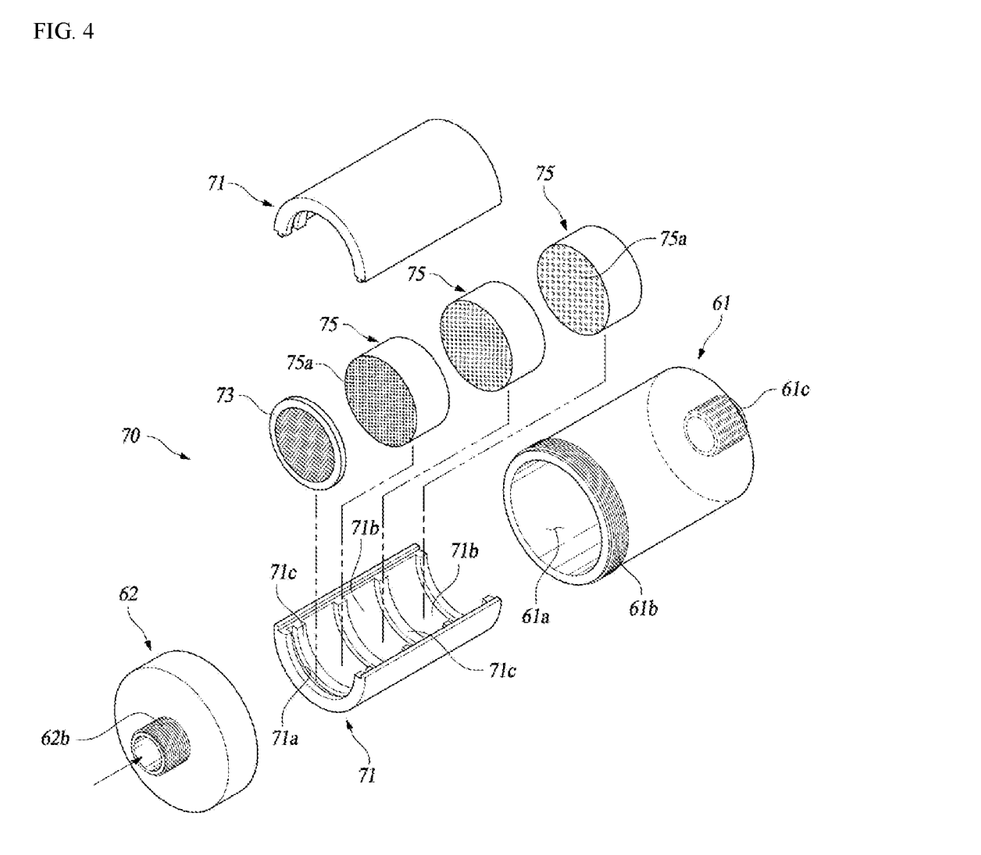
FIG. 4 is an exploded perspective view of the micro bubble generator of FIG. 3.
Figure 5:
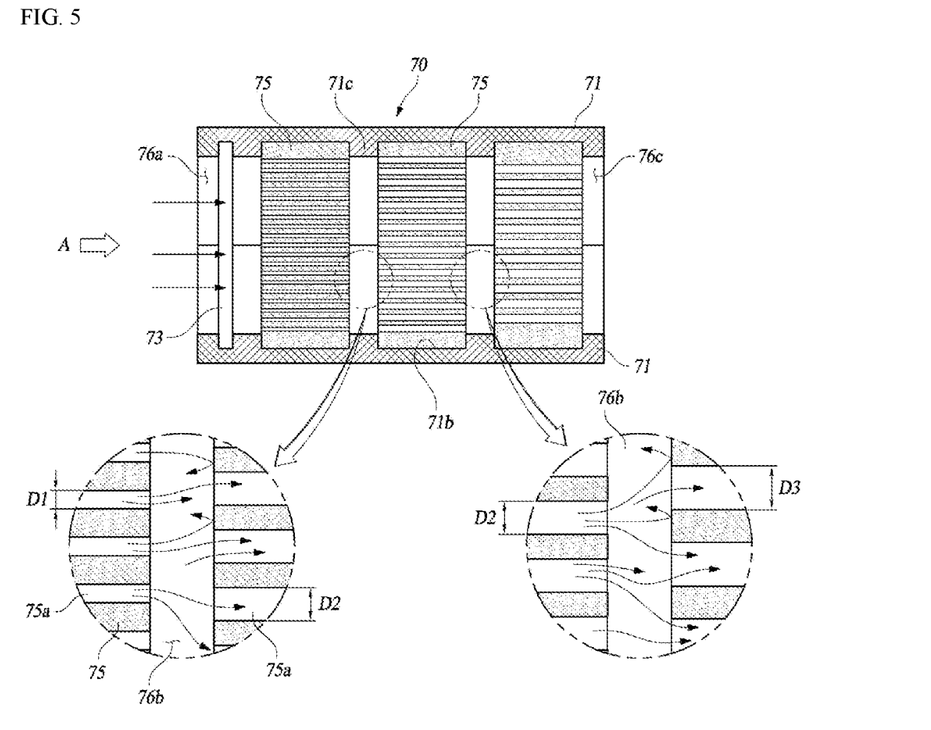
FIG. 5 is a view for illustrating an operating principle of a bubble generating cartridge shown in FIG. 4.
Figure 6:
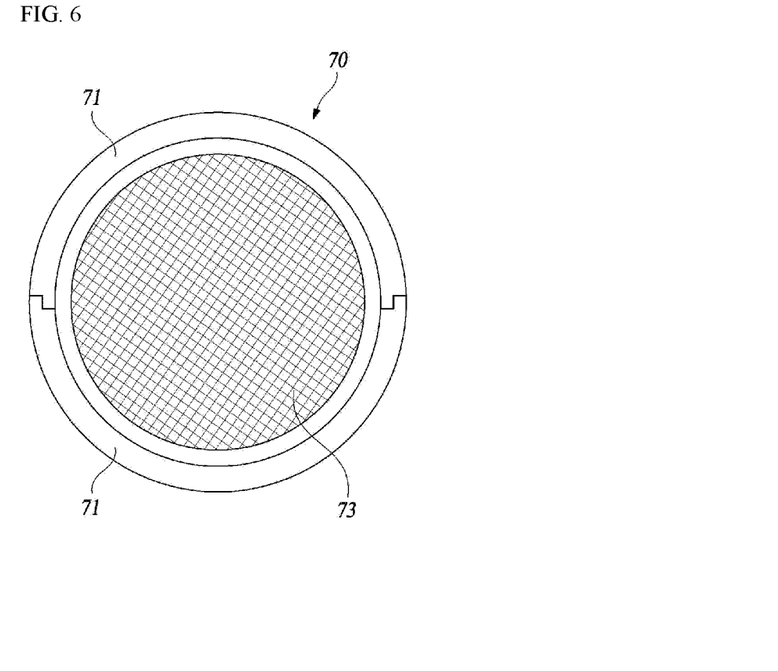
FIG. 6 is a view as viewed from the direction A of FIG. 5.

FIG. 2 is a block diagram illustrating a configuration of a micro bubble type ozone water supply 50 shown in FIG. 1, and FIG. 3 is a partially cut-away cross-sectional view illustrating an internal structure of the bubble generator 60 of FIG. 2. In addition, FIG. 4 is an exploded perspective view of the bubble generator of FIG. 3, FIG. 5 is a view for illustrating an operating principle of a bubble generating cartridge 70 shown in FIG. 4, and FIG. 6 is a view as viewed from the direction A of FIG. 5.

The micro bubble type ozone water supply 50 basically serves to inject and mix ozone into fresh water provided from the outside, dissolve ozone in the fresh water, and supply ozone water in which ozone is dissolved to the sterilization tub 20. Ozone water is water in which ozone is dissolved, and has the same sterilizing power as ozone. In particular, the micro bubble type ozone water supply 50 may increase a dissolution concentration of ozone in fresh water by passing fresh water and ozone therethrough so as to form micro bubbles.

As shown, the micro bubble type ozone water supply 50 includes a pressure pump 51, an ozone generator 53, a mixer 52, and a bubble generator 60.

The pressure pump 51 pumps provided fresh water toward the bubble generator 60. As shown in FIG. 5, a plurality of Teflon bodies 75 having micropores are mounted in series in the bubble generator 60, and pressurize water so that ozone water is capable of passing through the micropores at high speed.

The ozone generator 53 is the equipment for silently discharging clean dry air or oxygen. It is a known fact that ozone is produced by discharging oxygen. Ozone obtained by the discharging meets with water in the mixer 52 and starts to be dissolved in the water. The ozone is not 100% dissolved in the mixer 52, but is almost completely dissolved while passing through the bubble generator 60 in a gaseous state.

The bubble generator 60 has a function of completely dissolving ozone that has not yet been dissolved, by passing fresh water in which ozone gas is mixed therethrough so as to form bubbles, and produces high concentration ozone water by increasing a dissolution concentration of ozone in fresh water.

As shown in FIGS. 3 and 4, the bubble generator 60 consists of a housing 61, a bubble generating cartridge 70, and a sealing cap 62. The housing 61 has a space 61a for accommodating the bubble generating cartridge 70, and includes a cap fixing portion 61b on one side thereof and a hose connection portion 61c on the other side thereof. The cap fixing portion 61b is a portion to which the sealing cap 62 is coupled, and the hose connection portion 61c is a portion into which the hose 64 facing the sterilization tub 20 is screwed.

The sealing cap 62 seals the bubble generating cartridge 70 while coupled to the housing 61. The center of the sealing cap 62 is also provided with a hose connection 62b. The hose connection portion 62b is a portion into which the hose 63 connecting the mixer 52 and the bubble generating cartridge 70 is screwed.

The bubble generating cartridge 70 may include a pair of holding cases 71 that are mutually coupled and take the form of a cylinder, three Teflon bodies 75 disposed in the holding cases 71, and a filter 73 installed upstream of the Teflon bodies 75.

Each of the holding cases 71 is a semi-cylindrical member, and has a filter mounting groove 71a and three Teflon body mounting grooves 71b on an inner circumferential surface thereof. The filter mounting groove 71a is a groove into which the filter 73 is inserted, and the Teflon body mounting grooves 71b are grooves into which the Teflon bodies 75 are inserted.

Gap maintaining portions 71c are positioned between the filter mounting groove 71a and the Teflon body mounting groove 71b and between each of the Teflon body mounting grooves 71b. The gap maintaining portions 71c are ring-shaped protrusions that are naturally made by forming the filter mounting groove 71a and the Teflon mounting grooves 71b, and provide a decompression zone 76b between adjacent Teflon bodies 75. The decompression zone 76b is space in which water compressed by passing through the micropores 75a of the Teflon bodies 75 instantaneously expands, and will be described below.

The filter 73 serves to filter out fine contaminants from ozone water flowing into the bubble generator 60 that passes through the filter 73. Although the raw material of ozone water is fresh water and has no contaminants, the filter 73 is applied as a preventive measure. Naturally, the filter 73 may be omitted.

The Teflon bodies 75 are disk-shaped members having a predetermined diameter and thickness, and three Teflon bodies 75 are arranged in series. The Teflon bodies 75 are, of course, manufactured by processing a Teflon material. The number of Teflon bodies 75 to be applied may vary as needed. For example, only one Teflon body may be installed, or ten Teflon bodies may be installed. However, the further downstream the Teflon body is, the larger the inner diameter of the micropores 75a should be.

In addition, a plurality of micropores 75a are formed in each of the Teflon bodies 75. The micropores 75a are passageways extending parallel in the thickness direction of the Teflon bodies 75, and allow ozone water to pass therethrough. In particular, the inner diameter D1 of the micropores 75a of the upstream Teflon body 75, the inner diameter D2 of the micropores 75a of the intermediate Teflon body 75, and the inner diameter D3 of the micropores 75a of the downstream Teflon body are different from each other. The inner diameter sizes are D1<D2<D3. For example, D1 may be 0.10 mm, D2 may be 0.15 mm, and D3 may be 0.20 mm.

In the bubble generating cartridge 70 having this configuration, when ozone water flows into an inlet 76a, the ozone water passes through the filter 73 and then flows into the micropores 75a of the first Teflon body 75 and is compressed at high pressure at the same time. Since the total flow cross-sectional area of the micropores 75a is much smaller than the flow cross-sectional area of the inlet 76a and the ozone water is also continuously pressurized by the pressure pump 51, the flow velocity and pressure of the ozone water are bound to increase. In addition, molecules of ozone in a gaseous state that have not yet been dissolved are pressurized while passing through the micropores and are dissolved into water molecules.

The pressure of the ozone water that has passed through the first Teflon body 75 is greatly lowered as soon as it enters the decompression zone 76b, and the compressed gaseous ozone expands and bubbles. The bubbles collide with water, burst, and disappear, and in some cases, they encounter other bubbles and become larger and continuously dissolve in water.

The ozone water in the decompression zone 76b, in turn, passes through the Teflon body 75 located in the middle, then the decompression zone 76b and the third Teflon body 75, and is directed to the sterilization tub 20 through the outlet 76c in a state in which ozone is completely dissolved according to the principle described above.

Eventually, the concentration of ozone in fresh water is increased by the bubble generating cartridge 70. Of course, as the concentration of ozone increases, the sterilization power increases.

Figure 7A:
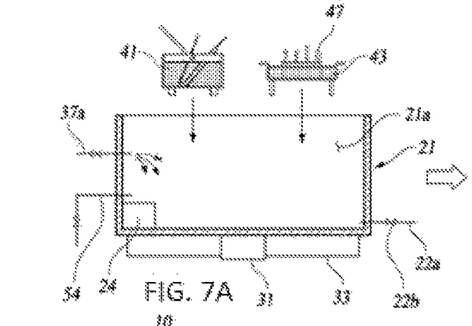
FIGS. 7A to 7G are diagrammatic views illustrating a method of sterilizing a treatment tool for a dental hospital according to an embodiment of the present disclosure.
Figure 7B:
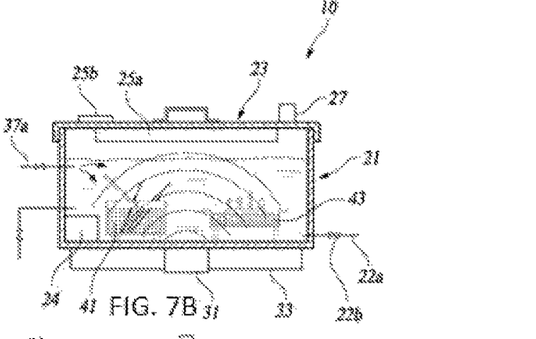
Figure 7C:
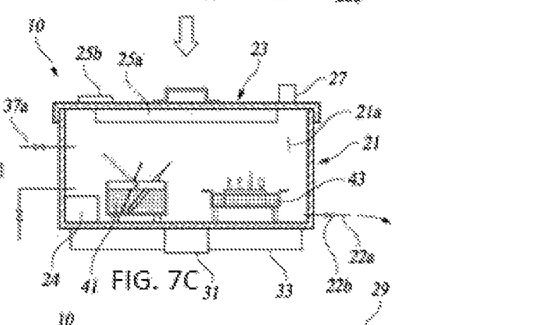
Figure 7D:
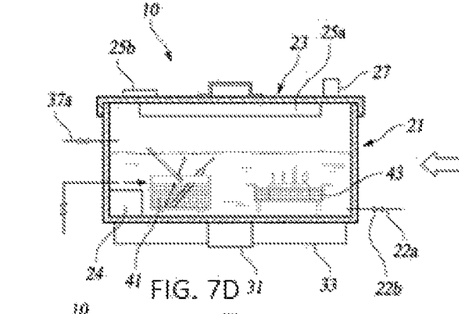
Figure 7E:
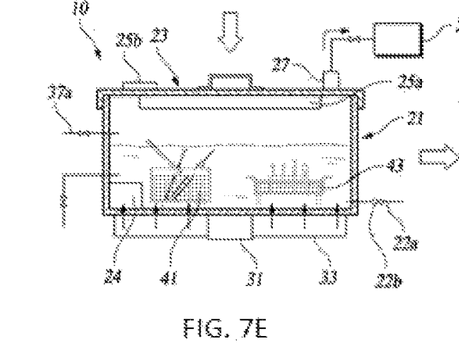
Figure 7F:
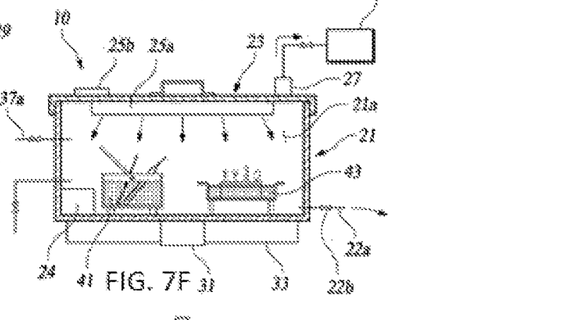
Figure 7G:
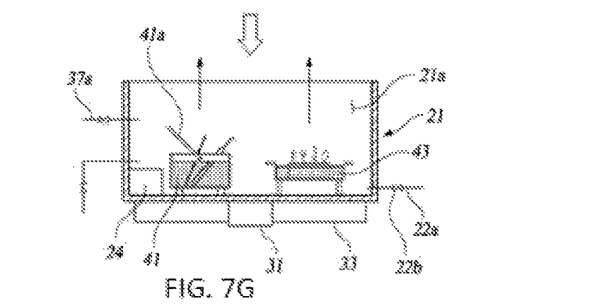
Figure 8:
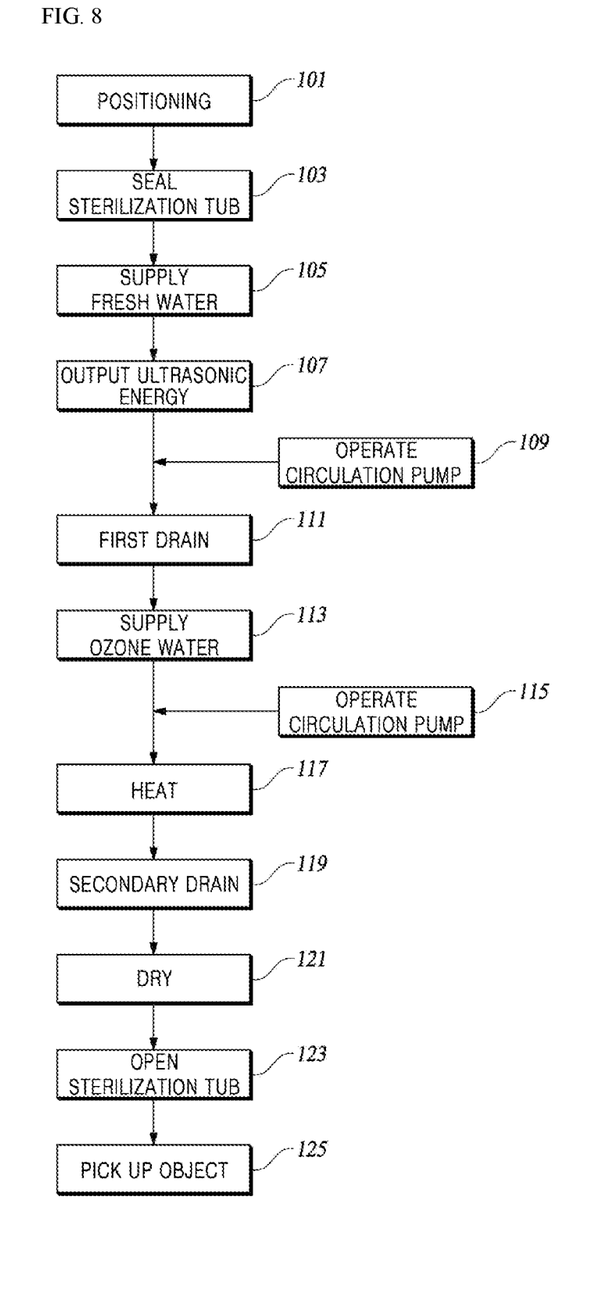
FIG. 8 is a flowchart of a method of sterilizing a treatment tool for a dental hospital according to an embodiment of the present disclosure.

FIGS. 7A to 7G are views for reference for illustrating how to use the sterilizer shown in FIG. 1, and FIG. 8 is a flow chart summarizing and illustrating how to use the sterilizer shown in FIG. 1.

As shown, the method of sterilizing a treatment tool for a dental hospital according to the present embodiment includes a positioning step 101, a sterilization tub sealing step 103, a fresh water supplying step 105, an ultrasonic energy outputting step 107, a circulation pump operating step 109, a first draining step 111, an ozone water supplying step 113, a circulation pump operating step 115, a heating step 117, a secondary draining step 119, a drying step 121, a sterilization tub opening step 123, and an object picking up step 125.

The positioning step 101 is a process of disposing the object to be sterilized, that is, the gripping tool 45 and the bur 47, into the container 21 with the top open. At this time, it is preferable that the gripping tool 45 and the bur 47 are put into or supported by the stainless steel basket 41 or the support tray 43 (see FIG. 7A).

Subsequently, the sterilization tub sealing step 103 is a process of sealing the accommodating space 21a of the container 21 by covering the top of the container 21 with the sealing cover 23. It is preferable to maintain a cleaner state by exhausting air from the accommodating space 21a while the sealing cover 23 is mounted.

The fresh water supplying step 105 is a process of filling the sterilizing tub 20 with fresh water by driving the fresh water supply 37, after the sterilizing tub 20 is sealed by the sealing cover 23. The level of fresh water is such that the object to be sterilized is completely immersed, as shown in FIG. 7B.

When the supply of fresh water through the fresh water supplying step 105 is completed, the ultrasonic energy outputting step 107 is performed. The ultrasonic energy outputting step 107 is a process of applying ultrasonic energy to fresh water by operating the ultrasonic generator 31 by the controller 35. The vibration energy of the ultrasonic energy applied to fresh water not only sterilizes bacteria, but also in particular elutes hardened blood or biological tissue embedded in the fine gaps of the bur 47 and separates bone tissue.

During the ultrasonic energy outputting step 107, the circulation pump operating step 109 may be performed. When the circulation pump 24 (see FIG. 1) is operated through the circulation pump operating step 109, fresh water in the sterilization tub 20 is rotated and agitated along the water stream in a certain direction by the circulation pump. The fresh water rotating in the sterilization tub 20 prevents fresh water around the object to be sterilized from stagnating. In other words, the dead bodies of bacteria do not float around the object to be sterilized.

Subsequently, the first draining step 111 is a process of opening the drain 22 to discharge used water to the outside. It has been mentioned above that the drain 22 is also controlled by the controller 35. When the first draining step 111 is completed, the interior of the sterilization tub 20 is emptied as shown in FIG. 7C.

If ultrasonic sterilization is further required while the sterilization tub 20 is empty, the fresh water supplying step 105, the ultrasonic energy outputting step 107, and the circulation pump operating step 109 may be repeated.

However, if ultrasonic sterilization has already been sufficiently performed, the ozone water supplying step 113 may then be performed. The ozone water supplying step 113 is a process of blocking the drain 22 and operating the ozone water supply 50. When the ozone water supply 50 is operated, ozone water is supplied into the sterilization tub 20. Since ozone water itself has a strong sterilizing power, it completely sterilizes bacteria that may remain on the surface of the object to be sterilized.

If necessary, the circulation pump operating step 115 may be performed even when the object to be sterilized is immersed in ozone water, as shown in FIG. 7D. When the ozone water rotates along a water stream in a certain direction, the activity of ozone may increase and sterilization efficiency may be improved.

When sterilization using ozone water is completed, the heating step 117 is performed. The heating step 117 is a process of heating ozone water by operating the heater 33. The heating temperature at this time is around 30° C. When ozone water is heated to this temperature, ozone in water is vaporized and converted into harmless oxygen.

In the heating step 117, it is preferable to operate the gas outlet 27 to more quickly discharge oxygen from the ozone water. When all ozone components have been removed through this process, the sterilization tub 20 is emptied through the secondary draining step 119.

Subsequently, the drying step 121 is a process of drying moisture on the sterilized gripping tool 45 and the bur 47 by operating the drying heater 25a, as shown in FIG. 7F. During the drying step 121, the gas outlet 27 is operated to discharge moisture. If sufficient drying has been achieved through the drying step 121, the sterilizing tub opening step 123 is performed. The sterilization tub opening step 123 is a process of turning off the drying heater 25a and opening the sealing cover 23.

When the sealing cover 23 is opened, the object picking up step 125 of lifting the stainless basket 41 in which the gripping tool 45 is contained and the support tray 43 on which the bur 47 is placed is performed, and then all processes are finished.

Above, the present disclosure has been described in detail through specific embodiments, but the present disclosure is not limited to the above embodiments, and various modifications are possible by those of ordinary skill within the sprit and the technical scope of the present disclosure.

What is claimed is:

1. A treatment tool sterilizer with a micro bubble type ozone water supply, comprising:
    a sterilization tub having a container configured to accommodate an object to be sterilized and a sealing cover covering the container and a circulation pump configured to stir accommodated fresh water or ozone water, the circulation pump in the sterilization tub;
    a fresh water supply configured to supply fresh water into the sterilization tub;
    a micro bubble type ozone water supply configured to supply ozone water for sterilization into the sterilization tub, wherein the micro bubble type ozone water supply comprises a pressure pump configured to pressurize and transfer fresh water provided from the outside, an ozone generator configured to generate ozone, a mixer configured to mix the ozone and fresh water transferred by the pressure pump, and a bubble generator connected to the mixer and configured to increase a dissolution concentration of ozone in fresh water by passing the fresh water and the ozone through the bubble generator so as to form micro bubbles;
    an ultrasonic generator configured to apply ultrasonic energy to the fresh water when the fresh water has been filled in the sterilization tub, so that the object to be sterilized immersed in the fresh water is sterilized by ultrasonic energy;
    a drain configured to discharge the fresh water from the sterilization tub;
    a heater mounted on the sterilization tub and configured to apply heat in the sterilization tub; and
    a controller configured to output a control signal.

2. The treatment tool sterilizer of claim 1, further comprising, in the sterilization tub, a drying heater configured to dry the object to be sterilized after draining the fresh water or the ozone water.

3. The treatment tool sterilizer of claim 1, wherein a stirrer configured to stir the accommodated fresh water or the ozone water is further provided in the sterilization tub.

4. The treatment tool sterilizer of claim 1, further comprising a basket or tray in a form of a mesh configured to accommodate the object to be sterilized, which is used when placing the object to be sterilized in the container.

5. A treatment tool sterilizer with a micro bubble type ozone water supply, comprising:
    a sterilization tub having a container configured to accommodate an object to be sterilized and a sealing cover covering the container;
    a fresh water supply configured to supply fresh water into the sterilization tub;
    a micro bubble type ozone water supply configured to supply ozone water for sterilization into the sterilization tub, wherein the micro bubble type ozone water supply comprises a pressure pump configured to pressurize and transfer fresh water provided from the outside, an ozone generator configured to generate ozone, a mixer configured to mix the ozone and fresh water transferred by the pressure pump, and a bubble generator connected to the mixer and configured to increase a dissolution concentration of ozone in fresh water by passing the fresh water and the ozone through the bubble generator so as to form micro bubbles;
    an ultrasonic generator configured to apply ultrasonic energy to the fresh water when the fresh water has been filled in the sterilization tub, so that the object to be sterilized immersed in the fresh water is sterilized by ultrasonic energy;
    a drain configured to discharge the fresh water from the sterilization tub;
    a heater mounted on the sterilization tub and configured to apply heat in the sterilization tub; and
    a controller configured to output a control signal,
    wherein the bubble generator comprises:
    a housing providing a space;
    a bubble generating cartridge mounted in the space of the housing and configured to pass a mixture of fresh water and ozone through the bubble generating cartridge so as to form micro bubbles; and
    a sealing cap coupled to the housing to fix the bubble generating cartridge in the housing.

6. The treatment tool sterilizer of claim 5,
    wherein the bubble generating cartridge comprises:
    a pair of holding cases that are mutually coupled and take a form of a cylinder in which both ends are opened,
    a Teflon body mounted in the pair of holding cases and having a plurality of micropores through which the mixture of fresh water and ozone passes, and a filter installed upstream of the Teflon body.

7. The treatment tool sterilizer of claim 6, wherein the Teflon body takes a form of a disk having a predetermined thickness, and a plurality of Teflon bodies are arranged in series to be spaced apart by a predetermined distance, and
    the plurality of micropores are formed in each of the plurality of Teflon bodies, wherein an inner diameter of each of the plurality of micropores is larger in downstream Teflon bodies than in upstream Teflon bodies.

8. A treatment tool sterilizer with a micro bubble type ozone water supply, comprising:
    a sterilization tub having a container configured to accommodate an object to be sterilized and a sealing cover covering the container;

a fresh water supply configured to supply fresh water into the sterilization tub; a micro bubble type ozone water supply configured to supply ozone water for sterilization into the sterilization tub, wherein the micro bubble type ozone water supply comprises a pressure pump configured to pressurize and transfer fresh water provided from the outside, an ozone generator configured to generate ozone, a mixer configured to mix the ozone and fresh water transferred by the pressure pump, and a bubble generator connected to the mixer and configured to increase a dissolution concentration of ozone in fresh water by passing the fresh water and the ozone through the bubble generator so as to form micro bubbles;

an ultrasonic generator configured to apply ultrasonic energy to the fresh water when the fresh water has been filled in the sterilization tub, so that the object to be sterilized immersed in the fresh water is sterilized by ultrasonic energy;

a drain configured to discharge the fresh water from the sterilization tub;

a heater mounted on the sterilization tub and configured to apply heat in the sterilization tub; and a controller configured to output a control signal, wherein a gas outlet configured to discharge gas generated from the fresh water or the ozone water out of the sterilization tub is provided on the sealing cover, and a collector configured to collect the gas discharged by the gas outlet is provided outside the sealing cover.

* * * * *